United States Patent
Sultana et al.

(10) Patent No.: US 6,989,444 B2
(45) Date of Patent: Jan. 24, 2006

(54) PROCESS FOR PRODUCING LACTAM

(75) Inventors: Asima Sultana, Kurashiki (JP); Hajime Nagahara, Kurashiki (JP); Yuichi Fujii, Kurashiki (JP); Ken Suzuki, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 100 days.

(21) Appl. No.: 10/488,238

(22) PCT Filed: Sep. 10, 2002

(86) PCT No.: PCT/JP02/09226

§ 371 (c)(1),
(2), (4) Date: Mar. 2, 2004

(87) PCT Pub. No.: WO03/024927

PCT Pub. Date: Mar. 27, 2003

(65) Prior Publication Data

US 2004/0215013 A1    Oct. 28, 2004

(30) Foreign Application Priority Data

Sep. 12, 2001  (JP) ............................. 2001-277005
Jul. 25, 2002   (JP) ............................. 2002-216371

(51) Int. Cl.
C07D 201/02    (2006.01)
(52) U.S. Cl. ..................................... 540/534
(58) Field of Classification Search ................. 540/534
See application file for complete search history.

(56)         References Cited

U.S. PATENT DOCUMENTS 4,337,358 A    6/1982    Armor

FOREIGN PATENT DOCUMENTS

EP    0 395 046 A2    10/1990

*Primary Examiner*—Bruck Kifle
(74) *Attorney, Agent, or Firm*—Birch, Stewart, Kolasch & Birch, LLP

(57)         ABSTRACT

A method for producing a lactam, which comprises subjecting an alicyclic primary amine to an oxidation reaction in the presence of a catalyst comprising a silicon oxide, to thereby obtain a lactam. A catalyst comprising a silicon oxide which is for use in the above-mentioned method.

24 Claims, No Drawings

PROCESS FOR PRODUCING LACTAM

BACKGROUND OF THE INVENTION

1. Field of the Invention

The present invention relates to a method for producing a lactam by oxidizing an alicyclic primary amine. More particularly, the present invention is concerned with a method for producing a lactam, which comprises subjecting an alicyclic primary amine to an oxidation reaction in the gaseous phase in the presence of molecular oxygen and a catalyst comprising a silicon oxide, to thereby obtain a lactam, and separating the lactam from a reaction system of the oxidation reaction. In addition, the present invention also relates to a catalyst comprising a silicon oxide, which is for use in the above-mentioned method. The method of the present invention not only prevents the by-production of ammonium sulfate which is of little commercial value, but also needs no cumbersome operations involved in conventional methods for producing a lactam, such as synthesis of hydroxylamine salt (which can be obtained only by a process involving complicated steps) and circulation of a buffer solution, and involves no step of producing an intermediate oxime, which should be followed by an oxime purification operation, and, hence, a lactam can be produced from an alicyclic primary amine very easily.

2. Prior Art

In the field of organic chemical industry, lactams are compounds useful as raw materials for polymers, pharmaceuticals, agricultural chemicals and the like. In the case of $\epsilon$-caprolactam, this compound has been used for producing fibers and resins, and is especially useful as a raw material for nylon 6.

Various processes for producing lactams, such as $\epsilon$-caprolactam, are conventionally known. As examples of such conventional processes, there can be mentioned the processes described in "Kougyou Yuuki Kagaku (Industrial Organic Chemistry)", fourth edition, page 240 (1976), written by von Klaus Weissermel and Hans-Jurgen Arpe, translated under supervision of Teruaki Mukaiyama, TOKYO KAGAKU DOZIN CO., LTD., Japan (von Klaus Weissermel und Hans-Jurgen Arpe, "INDUSTRIELLE ORGANISCHE CHEMIE", Verlag Chemie Gmbh (1976)), which processes include:

(A) cyclohexanone oxime process in which cyclohexanone oxime is synthesized directly or through an intermediate compound (cyclohexanone) from cyclohexane, and the synthesized cyclohexanone oxime is subjected to Beckman rearrangement, to thereby obtain $\epsilon$-caprolactam;

(B) cyclohexanecarboxylic acid process in which toluene is oxidized in air to produce benzoic acid, the produced benzoic acid is hydrogenated to produce cyclohexanecarboxylic acid, and the produced cyclohexanecarboxylic acid is reacted with nitrosylsulfuric acid in the presence of fuming sulfuric acid, to thereby obtain $\epsilon$-caprolactam;

(C) caprolactone process in which cyclohexanone is oxidized with peracetic acid to produce $\epsilon$-caprolactone, and the produced $\epsilon$-caprolactone is reacted with ammonia to thereby obtain $\epsilon$-caprolactam; and (D) nitrocyclohexanone process in which cyclohexanone is acetylated to obtain cyclohexenyl acetate, the obtained cyclohexenyl acetate is nitrated to obtain 2-nitrocyclohexanone, the obtained 2-nitrocyclohexanone is subjected to hydrolysis, thereby causing ring cleavage of the 2-nitrocyclohexanone to obtain nitrocapronic acid, the obtained nitrocapronic acid is hydrogenated to obtain $\epsilon$-aminocapronic acid, and the obtained $\epsilon$-aminocapronic acid is converted into $\epsilon$-caprolactam.

Among the above-mentioned processes (A) to (D), the cyclohexanone oxime process (A) and the cyclohexane carboxylate process (B) have been practiced on a commercial scale. Especially, the cyclohexanone oxime process (A) has been practiced worldwide and is the most important.

The representative method for producing a lactam by the cyclohexanone oxime process is a method in which cyclohexanone oxime is produced from cyclohexanone and a hydroxylamine salt and, then, $\epsilon$-caprolactam is synthesized from the produced cyclohexanone oxime by the Beckman rearrangement performed using sulfuric acid. The Raschig process, which is a classical oximation process, involves the steps of reducing ammonium nitrate using $SO_2$ to obtain a disulfonate, and hydrolyzing the obtained disulfonate to obtain a hydroxylamine salt of sulfuric acid salt. The Raschig process practiced on a commercial scale involves four steps which are very complicated. Further, in this process, the amount of ammonium sulfate by-produced during the oximation performed using the above-mentioned hydroxylamine salt of sulfuric acid salt is approximately two moles per mole of the finally produced lactam. When the amount of ammonium sulfate by-produced in the Beckman rearrangement performed using sulfuric acid is also taken into consideration, the amount of ammonium sulfate by-produced in the Raschig process is approximately four moles per mole of the finally produced lactam. The commercial value of ammonium sulfate as a raw material for a fertilizer is no longer high, and the necessity of disposal of the by-produced ammonium sulfate is a great disadvantage of this process.

In this situation, for suppressing the by-production of ammonium sulfate, the hydroxylamine sulfate oxime process (HSO process) and the hydroxylamine phosphate oxime process (HPO process) have been proposed.

The HSO process (see, for example, U.S. Pat. Nos. 3,941,838 and 4,031,139) involves oxidizing ammonia in the presence of a platinum-containing catalyst to obtain NO, subjecting the obtained NO to reduction with hydrogen in the presence of a platinum-containing catalyst using an ammonium hydrogensulfate/ammonium sulfate buffer solution to produce hydroxylammonium sulfate, and reacting the produced hydroxylammonium sulfate with cyclohexanone.

The HPO process (see, for example, U.S. Pat. Nos. 3,948,988 and 3,940,442) involves oxidizing ammonia to obtain a nitric acid ion, subjecting the obtained nitric acid ion to reduction with hydrogen in the presence of palladium as a catalyst using a phosphoric acid/monoammonium phosphate buffer solution to produce a hydroxylamine salt of phosphoric acid, and reacting the produced hydroxylamine salt of phosphoric acid with cyclohexanone.

Each of the above-mentioned HSO and HPO processes is advantageous in that the buffer solution is allowed to circulate between the cyclohexanone oxime production system and the hydroxylamine salt production system, so that by-production of ammonium sulfate can be prevented. However, each of the processes has the following disadvantages. The process involves a number of reaction steps. Furthermore, the step of circulating the buffer solution is complicated.

As another improved process, there is known a process involving reacting cyclohexanone with ammonia and hydrogen peroxide in the presence of a solid catalyst to obtain cyclohexanone oxime (see U.S. Pat. No. 4,745,221). This method is advantageous not only in that the production of hydroxylamine salt is not needed and, hence, the circulation of the buffer solution is not needed, but also in that ammonium sulfate is not by-produced. However, in this method, although the oximation is not accompanied by the by-production of ammonium sulfate, ammonium sulfate is by-produced during the synthesis of a lactam as long as the Beckman rearrangement of an oxime for obtaining ε-caprolactam is performed using sulfuric acid.

Cyclohexanone oxime processes involving no step of producing intermediate cyclohexanone have also been practiced. As an example of such processes, there can be mentioned the photo-nitrosylation process which involves reacting cyclohexane with a gaseous mixture of hydrogen chloride and nitrosyl chloride by light irradiation using a mercury lamp to obtain an oxime. This method is advantageous in that ammonium sulfate is not by-produced. However, the method has the following disadvantages. Light is needed for the oximation, so that not only is a large amount of power needed for the oximation, but also maintenance of a mercury lamp or the like used for irradiation of light is cumbersome.

As another example of the cyclohexanone oxime processes involving no step of producing intermediate cyclohexanone, there can be mentioned a method which comprises subjecting cyclohexylamine to oxidation in the presence of a catalyst in the liquid or gaseous phase to thereby obtain cyclohexanone oxime. This method is advantageous in that ammonium sulfate is not by-produced.

However, although this method is not accompanied by the by-production of ammonium sulfate during the oximation step, ammonium sulfate is by-produced during the synthesis of a lactam as long as the Beckman rearrangement of an oxime for obtaining ε-caprolactam is performed using sulfuric acid.

In this situation, several attempts have been made to prevent the by-production of ammonium sulfate during the Beckman rearrangement. For example, a gaseousphase Beckman rearrangement reaction using a solid catalyst is known as a Beckman rearrangement reaction which is free from the by-production of ammonium sulfate. In most cases, the gaseous-phase Beckman rearrangement reaction is performed by a method in which an oxime is converted to ε-caprolactam in the gaseous phase in the presence of a zeolite type catalyst in a fixed-bed reactor or fluidized-bed reactor. In this method, ammonium sulfate is not by-produced because sulfuric acid is not used.

By combining the above-mentioned conventional processes, for example, by combining the oximation of cyclohexanone using hydrogen peroxide and the gaseousphase Beckman rearrangement of the resultant oxime, it is possible to obtain a method for producing a lactam, which is free from the by-production of ammonium sulfate and cumbersome operations, such as synthesis of hydroxylamine salts and circulation of a buffer solution, and which does not consume a large amount of electricity for providing light energy to the reaction system. However, the above-mentioned method comprising the conventional processes has the following disadvantages. In this method, the production of the intermediate oxime necessitates a purification process for oxime. In other words, the solvent used in the oximation process, unreacted ammonia and by-produced water must be separation-removed from the oximation reaction mixture before subjecting the produced oxime to the gaseous-phase Beckman rearrangement. In addition, the solid catalyst used for the gaseous-phase Beckman rearrangement reaction is likely to be poisoned by impurities by-produced in a trace amount and, therefore, a high degree purification of the oxime becomes necessary.

Thus, there has been no conventional method for producing a lactam, which is free from the by-production of ammonium sulfate and the necessity for cumbersome operations, such as synthesis of hydroxylamine salts and circulation of a buffer solution, and which needs no oxime purification operation (i.e., which involves no step of producing an intermediate oxime).

SUMMARY OF THE INVENTION

In this situation, the present inventors have made extensive and intensive studies with a view toward developing a method which is free from the above-mentioned problems. As a result, it has surprisingly been found that the above-mentioned problems can be solved by a method for producing a lactam, which comprises subjecting an alicyclic primary amine to an oxidation reaction in the gaseous phase in the presence of molecular oxygen and a catalyst comprising a silicon oxide, to thereby obtain a lactam, and separating the lactam from a reaction system of the oxidation reaction. Based on this finding, the present invention has been completed.

Accordingly, it is an object of the present invention to provide a method for producing a lactam, which solves the above-mentioned problems and enables a very easy production of a lactam directly from a raw material alicyclic primary amine without producing an intermediate oxime, wherein the method not only is free from the by-production of ammonium sulfate which is of little commercial value, but also needs no cumbersome operations involved in conventional methods for producing a lactam, such as synthesis of hydroxylamine salt (which can be obtained only by a process involving complicated steps), circulation of a buffer solution) and oxime purification operation.

It is another object of the present invention to provide a catalyst for use in the above-mentioned method, which comprises a silicon oxide.

The foregoing and other objects, features and advantages of the present invention will be apparent from the following detailed description and appended claims.

DETAILED DESCRIPTION OF THE INVENTION

In one aspect of the present invention, there is provided a method for producing a lactam, which comprises subjecting an alicyclic primary amine to an oxidation reaction in the gaseous phase in the presence of molecular oxygen and a catalyst comprising a silicon oxide, to thereby obtain a lactam, and separating the lactam from a reaction system of the oxidation reaction.

In another aspect of the present invention, there is provided a catalyst for use in producing a lactam by subjecting an alicyclic primary amine to an oxidation reaction, which comprises a silicon oxide.

For easy understanding of the present invention, the essential features and various preferred embodiments of the present invention are enumerated below.

1. A method for producing a lactam, which comprises subjecting an alicyclic primary amine to an oxidation reaction in the gaseous phase in the presence of molecular oxygen and a catalyst comprising a silicon oxide, to thereby obtain a lactam, and separating the lactam from a reaction system of the oxidation reaction.

5. The method according to item 1 above, wherein the catalyst further comprises at least one element selected from the group consisting of lithium, sodium, potassium, rubidium, cesium, magnesium, calcium, strontium, barium, titanium, zirconium, vanadium, niobium, tantalum, molybdenum, tungsten, manganese, iron, cobalt, nickel, copper, zinc, silver, boron, aluminum, gallium, tin, phosphorus, antimony and bismuth.

6. The method according to item 1 above, wherein the catalyst is a zeolite.

7. The method according to item 6 above, wherein the zeolite is selected from the group consisting of silicalite-1 and silicalite-2.

8. The method according to item 1 above, wherein the catalyst comprises an amorphous silicon oxide as the silicon oxide.

9. The method according to item 8 above, wherein the catalyst further comprises aluminum.

10. The method according to item 8 above, wherein the amorphous silicon oxide has mesopores.

11. The method according to item 10 above, wherein the amorphous silicon oxide having mesopores is selected from the group consisting of MCM-41 and HMS.

12. The method according to item 10 above, wherein the amorphous silicon oxide having mesopores is produced by adding to a silicon alkoxide a quaternary ammonium salt.

13. The method according to item 12 above, wherein the quaternary ammonium salt is cetyltrimethylammonium salt.

14. The method according to any one of items 1 and 5 to 13 above, wherein the alicyclic primary amine is obtained by subjecting to an amination reaction at least one compound selected from the group consisting of an alicyclic alcohol and an alicyclic ketone.

15. The method according to item 14 above, wherein at least a part of one or more by-products formed in the oxidation reaction is recycled to a reaction system of the amination reaction.

16. The method according to item 1 above, wherein the alicyclic primary amine is cyclohexylamine, and the lactam is ε-caprolactam.

17. The method according to item 14 above, wherein the at least one compound selected from the group consisting of an alicyclic alcohol and an alicyclic ketone is selected from the group consisting of cyclohexanol and cyclohexanone, the alicyclic primary amine is cyclohexylamine, and the lactam is ε-caprolactam.

18. A catalyst for use in producing a lactam by subjecting an alicyclic primary amine to an oxidation reaction, which comprises a silicon oxide.

19. The catalyst according to item 18 above, which further comprises at least one element selected from the group consisting of lithium, sodium, potassium, rubidium, cesium, magnesium, calcium, strontium, barium, titanium, zirconium, vanadium, niobium, tantalum, molybdenum, tungsten, manganese, iron, cobalt, nickel, copper, zinc, silver, boron, aluminum, gallium, tin, phosphorus, antimony and bismuth.

20. The catalyst according to item 18 above, which is a zeolite.

21. The catalyst according to item 20 above, which is a zeolite selected from the group consisting of silicalite-1 and silicalite-2.

22. The catalyst according to item 18 above, which comprises an amorphous silicon oxide as the silicon oxide.

23. The catalyst according to item 22 above, which further comprises aluminum.

24. The catalyst according to item 22 above, wherein the amorphous silicon oxide has mesopores.

25. The catalyst according to item 24 above, wherein the amorphous silicon oxide having mesopores is selected from the group consisting of MCM-41 and HMS.

26. The catalyst according to item 24 above, wherein the amorphous silicon oxide having mesopores is produced by adding to a silicon alkoxide a quaternary ammonium salt.

27. The catalyst according to item 26 above, wherein the quaternary ammonium salt is cetyltrimethylammonium salt.

As explained above, several processes for producing a cycloalkanone oxime by oxidizing an alicyclic primary amine have been known in the art.

As examples of conventional processes for oxidation of cyclohexylamine using molecular oxygen as an oxidizing agent, there can be mentioned a process in which the oxidation of cyclohexylamine is performed in the liquid phase using, as a catalyst, a compound of at least one metal selected from the group consisting of metals belonging to Group 4 (IVB) of the Periodic Table (i.e., Ti, Zr and Hf) (see Unexamined Japanese Patent Application Laid-Open Specification No. Hei 2-295956 (corresponding to EP 395046)); and a process in which the oxidation of cyclohexylamine is performed in the gaseous phase in the presence of a solid catalyst comprising $SiO_2$ gel, $\gamma$-$Al_2O_3$, and optionally $WO_3$ (see U.S. Pat. Nos. 4,337,358 and 4,504,681).

As examples of conventional processes for oxidation of cyclohexylamine using hydrogen peroxide as an oxidizing agent, there can be mentioned a process using a catalyst comprising at least one metal selected from the group consisting of Mo, W and U (see U.S. Pat. No. 2,706,204); and a process in which a titanium silicalite or a vanadium silicalite is used as a catalyst (see Tetrahedron, Vol. 51 (1995), No. 41, page 11305; and Catal. Lett., Vol. 28 (1994), page 263).

Further, as examples of conventional processes for oxidation of cyclohexylamine using an organic hydroperoxide as an oxidizing agent, there can be mentioned a process using a catalyst comprising at least one metal selected from the group consisting of Ti, V, Cr, Se, Zr, Nb, Mo, Te, Ta, W, Re and U (see U.S. Pat. No. 3,960,954).

However, none of the above-mentioned prior art documents describe that ε-caprolactam is formed by the above-mentioned methods. Therefore, the production of a lactam directly from an alicyclic primary amine by oxidation was conventionally not known.

The present inventors have for the first time found that a lactam can be produced directly from an alicyclic primary amine without producing an intermediate cycloalkanone oxime, and successfully developed a method for producing a lactam which not only is free from the by-production of ammonium sulfate, but also needs no cumbersome operations including an oxime purification operation. Such a method is a very useful technique because it leads to a decrease in the cost for the lactam production operation as well as the cost for the lactam production facilities.

Hereinbelow, the present invention is described in detail.

It is preferred that the alicyclic primary amine used in the method of the present invention is a saturated alicyclic primary amine. Specific examples of saturated alicyclic primary amines include cyclohexylamine, cyclooctylamine, cyclopentylamine, cycloheptylamine and cyclododecanylamine. Among them, cyclohexylamine is preferred. Further, an alicyclic group of the alicyclic primary amine may be substituted with a substituent which is inert under the reaction conditions employed in the method of the present invention. One example of such an inert substituent is an alkyl group. The alicyclic primary amine may be substituted with one or more substituents. As an example of alicyclic primary amines substituted with an alkyl group, there can be mentioned methylcyclohexylamine.

Cyclohexylamine, which is a preferred alicyclic primary amine, can be produced by, for example, any of the following processes: direct amination of cyclohexene with $NH_3$ (e.g., processes described in Unexamined Japanese Patent Application Laid-Open Specification No. Sho 57-4948 (corresponding to EP 39918), Unexamined Japanese Patent Application Laid-Open Specification No. Sho 64-75453 (corresponding to EP 305564), Unexamined Japanese Patent Application Laid-Open Specification No. Hei 9-194438 (corresponding to EP 785185), Unexamined Japanese Patent Application Laid-Open Specification No. Hei 10-72409 (corresponding to EP 802176), and Unexamined Japanese Patent Application Laid-Open Specification No. Hei 10-291968 (corresponding to EP 846675)); amination of cyclohexanol with $NH_3$ (e.g., processes described in Examined Japanese Patent Application Publication No. Sho 41-7575, Examined Japanese Patent Application Publication No. Sho 51-41627, Examined Japanese Patent Application Publication No. Sho 51-32601 (corresponding to U.S. Pat. No. 3,520,933) and Unexamined Japanese Patent Application Laid-Open Specification No. Hei 6-1758); amination of cyclohexanone with $NH_3$ (e.g., processes described in Examined Japanese Patent Application Publication No. Sho 43-4332, Examined Japanese Patent Application Publication No. Sho 45-19897 (corresponding to U.S. Pat. No. 3,519,061), Examined Japanese Patent Application Publication No. Sho 45-19898); and hydrogenation of aniline, nitrobenzene, nitrocyclohexane or the like.

With respect to the purity of cyclohexylamine, there is no particular limitation, and the cyclohexylamine used in the present invention may contain a trace amount of any of organic compounds, such as cyclohexanol, dicyclohexylamine, nitrocyclohexane and N-cyclohexylidene-cyclohexylamine, which are formed during various synthesis processes involved in the cyclohexylamine production, and/or a trace amount of water.

From the viewpoint of economical advantages, molecular oxygen is preferred as an oxidizing agent used in the oxidation reaction performed in the method of the present invention. However, the oxidizing agent is not limited to molecular oxygen. If desired, any other oxidizing agents may be used as the oxidizing agent. Examples of other oxidizing agents include various peroxides, such as hydrogen peroxide and tertiary peroxide.

The method of the present invention is performed in the presence of a catalyst comprising a silicon oxide. It is preferred that the catalyst further comprises at least one element selected from the group consisting of lithium, sodium, potassium, rubidium, cesium, magnesium, calcium, strontium, barium, titanium, zirconium, vanadium, niobium, tantalum, molybdenum, tungsten, manganese, iron, cobalt, nickel, copper, zinc, silver, boron, aluminum, gallium, tin, phosphorus, antimony and bismuth. In the present invention, the above-mentioned "at least one element" is frequently referred to as a "heterometal". Among the above-mentioned heterometals, aluminum is especially preferred.

Further, the catalyst may comprise a trace amount of impurities which are derived from the raw materials used for producing the catalyst.

With respect to the structure of the catalyst, the silicon oxide as a main component of the catalyst may have a crystalline structure or an amorphous structure.

A zeolite can be used as the catalyst comprising a crystalline silicon oxide. Zeolites can be classified into natural zeolites and synthetic zeolites, depending on the formation process thereof. Both natural and synthetic zeolites can be used as a catalyst in the present invention. Conventionally, the term "zeolite" is used as a generic term for crystalline aluminosilic acid (alluminosilicate), but the zeolite as defined in the present invention also encompasses a compound comprising substantially no aluminum and composed only of a silicon oxide (e.g., silicalite), a compound further comprising metal components other than aluminum (e.g., metallosilicate) and the so-called "phosphate zeolite".

Specific examples of natural zeolites include natrolite, gonnardite, edingtonite, analcime, leucite, yugawaralite, gismondine, paulingite, phillipsite, chabazite, erionite, faujasite, mordenite, ferrierite, mutinaite, tshernichite, heulandite, clinoptilolite, stilbite, cowlesite, roggianite, hsianghualite, gaultite, pahasapaite and weinebeneite.

Specific examples of synthetic zeolites include an A type zeolite, ZK-4, ZK-21, ZSM-5, ZSM-11, ZSM-12, silicalite-1, silicalite-2, a β type zeolite, an X type zeolite, a Y type zeolite, EU-1, NU-87, UTD-1, CIT-5, ITQ-4, ITQ-7, SSZ-42, MCM-21, MCM-22, TS-1, TS-2, VS-1, VS-2, tantalum silicate, SAPO-11, SAPO-34, SAPO-37, SAPO-42 and SAPO-56. The zeolite may have a heterometal incorporated into the skeletal lattice thereof or may contain a heterometal outside the skeletal lattice thereof. As a general method for introducing a heterometal into the skeletal lattice of a zeolite, there can be mentioned a method in which a heterometal is added to the raw materials for the zeolite. As a general method for obtaining a zeolite containing a heterometal outside the skeletal lattice, there can be mentioned an impregnation method.

Among the above-mentioned zeolites, silcalite-1 and silicalite-2 are preferred.

With respect to silicalite-1, the synthesis method and crystal structure have been reported by Flanigen et al. (see E. M. Flanigen et al., Nature, Vol. 271, p. 512 (1978)). Silicate-1 has an MFI structure as in the case of ZSM-5 which is an aluminosilicate. ZSM-5 comprises a unit cell having a structure represented by the formula: $Na_n[Al_nSi_{96-n}O_{192}] \cdot xH_2O$, and silicate-1 is a compound comprising a unit cell which is substantially the same as that of ZSM-5, except that Al is not contained therein. ZSM-5 has linear channels (pores formed by 10-membered rings having a diameter of from 0.56 nm to 0.53 nm) extending along the b-axis and zigzag channels (pores formed by 10-membered rings having a size of from 0.55 nm to 0.51 nm) extending along the a-axis, wherein the linear channels and zigzag channels are interconnected with each other to thereby form a three-dimensional channel system.

As an example of the method for producing silicalite-1, which is based on the technique described in the above-mentioned document, there can be mentioned a method comprising mixing tetraethoxysilane, ethanol and hydrous tetrapropylammonium hydroxide to thereby obtain a mixture, and subjecting the obtained mixture to a hydrothermal synthesis at 100 to 200° C.

With respect to silicalite-2, the synthesis method and crystal structure have been reported by Bibby et al. (see D. M. Bibby et al., Nature, Vol. 280, p. 664 (1979)). Silicate-2 has the MEL structure as in the case of ZSM-11. The composition of the unit cell of ZSM-11 is the same as that of ZSM-5, and ZSM-11 also has channels formed by 10-membered rings; however, unlike ZSM-5, both of the channels extending along the a-axis and the channels extending along the b-axis are linear. Silicalite-2 has substantially the same structure as that of ZSM-11, except that Al is not contained therein.

As an example of the method for producing silicalite-2, which is based on the technique described in the above-mentioned document, there can be mentioned a method comprising providing a silicon oxide hydrate or teraethoxysilane as an Si source and tetrabutylammonium hydroxide as a template, and subjecting the Si source and the template to a hydrothermal synthesis at around 170° C. The use of tetrabutylammonium hydroxide is important for synthesizing silicalite-2, because silicalite- 2 cannot be synthesized using any of other ammonium hydroxides, such as tetraethylammonium hydroxide, tetrapropylammonium hydroxide, triethylpropylammonium hydroxide and triethylbutylammonium hydroxide.

With respect to the catalyst used in the method of the present invention, which comprises an amorphous silicon oxide, it is preferred that the amorphous silicon oxide has the so-called "mesopores". The term "pores" herein means small voids present on the surface of the catalyst or inside the catalyst. With respect to the classification of the pores, it has been internationally agreed to classify the pores into the following categories, based on the pore diameter thereof: submicropores (pore diameter<0.8 nm), micropores (0.8 nm<pore diameter<2 nm), mesopores (2 nm<pore diameter<50 nm) and macropores (pore diameter>50 nm) (see IUPAC-Manual of Symbols and Terminology for Physicochemical Quantities and Units, Butterworths, London (1972)). In the method of the present invention, among the catalysts comprising an amorphous silicon oxide having mesopores, it is preferred to use a catalyst having a narrow pore diameter distribution, namely a catalyst generally called a "mesoporous substance"(see Ono and Yajima ed., "Zeoraito no Kagaku to Kougaku (Science and Technology of Zeolites)", page 13, 2000, published by Koudansha Scientific, Japan). A mesoporous substance is a substance having pores which are larger than those of a microporous substance (such as a zeolite) and smaller than those of a macroporous substance, and it is characteristic of a mesoporous substance that, as mentioned above, the pore diameter is in the range of from 2 to 50 nm, and that the pore diameter distribution is narrow such that the diameters of the pores are almost the same.

The pore diameter distribution can be determined by various methods, such as mercury porosimetry and gas adsorption method. With respect to the determination of the pore diameter distribution of mesopores, it is generally considered to be appropriate to employ specific gas adsorption methods, such as the BJH method, the DH method and the MP method. The BJH method is employed in the Working Examples of the present invention. In the BJH method, the pore diameter distribution of a porous substance is calculated from the gas adsorption isotherm on the assumption that all of the pores of the porous substance are cylindrical. Specifically, the pore diameter distribution is determined, based on the peak profile of the differential distribution curve obtained from the data of the gas adsorption isotherm. For those who have ordinary skill in the field where porous substances are used as a catalyst etc., the BJH method is a very popular method for determining the pore diameter distribution of a mesoporous substance. For example, the BJH method is described in S. J. Gregg and K. S. W. Sing, "Adsorption, Surface Area and Porosity", Academic Press, London (1982). Further, it is characteristic of a mesoporous substance that, in a powder x-ray diffraction analysis of the substance, a sharp peak is observed at around 2 to 3 in terms of the 2θ/deg value. Such mesoporous materials include FSM-16, MCM-41, MCM-48, MCM-50, SBA-1, SBA-2, SBA-3, HMS, MSU-1, MSU-2, SBA-11, SBA-12, MSU-V, MSU-3, SBA-15 and SBA-16.

One of the generally employed methods for preparing a mesoporous substance involves reacting a lamellar silicate with a mono(long chain alkyl)tri(short chain alkyl)ammonium salt, such as a cetyltrimethylammonium salt. For example, FSM-16 can be produced by this method from kanemite which is a lamellar silicate. It is understood that a mono(long chain alkyl)tri(short chain alkyl)ammonium salt is intercalated between the layers of lamellar silicate and widens the spaces between the layers, thereby forming mesopores.

Another method for preparing a mesoporous substance involves reacting a silica source, such as a silicate or an alkoxide, with a surfactant (which is called a "template" for producing a mesoporous substance), to thereby obtain an organic-inorganic mesostructure in which the silica source molecules are arranged around meso-size micelles of the surfactant. Although it depends on the type of the mesostructure, it is generally necessary to subject a mixture of the silica source and the template to aging for a certain period of time to form the organic-inorganic mesostructure. As a template, it is possible to use not only a surfactant (such as an anionic surfactant, a cationic surfactant or a nonionic surfactant), but also an alkylamine, an alkyldiamine or the like. The template contained in a mesostructure can be decomposed and removed by solvent extraction or calcination to thereby obtain a mesoporous substance.

Among the above-mentioned catalysts which are mesoporous substances, MCM-41 and HMS are preferred. MCM-41 is a mesoporous silica which was reported by Mobil Oil Company in 1992 (see C. T. Kresge et al., Nature, 359, 710 (1992)). As a method for producing a MCM-41 having mesopores which are regularly arranged in a manner similar to the arrangement of beehive holes, there can be mentioned a method in which a silicon alkoxide (such as tetraethoxysilane) or $SiO_2$ is used as an Si source and a quaternary ammonium salt having a long chain alkyl group (such as cetyltrimethylammonium bromide) is used as a template, and the Si source and the template are subjected to a hydrothermal synthesis at 150° C. for 48 hours.

With respect to HMS, the synthesis method and structure were reported by Tanev et al. (see P. T. Tanev et al., Science, Vol. 267, p. 865 (1995)). The difference between the method for synthesizing MCM-41 and the method for synthesizing HMS is that HMS is synthesized using an alkylamine as a template. In the above-mentioned document, the aging in the synthesis of HMS is performed at room temperature for 18 hours.

The template contained in the catalyst can be removed as follows. In the case of MCM-41, a quaternary ammonium salt (template) can be heat-decomposition removed by calcining MCM-41. In the case of HMS, an amine (template) can be extraction removed from HMS using ethanol and the like and, therefore, HMS is advantageous in that the template can be recovered and recycled. HMS is also called a mesoporous silica having a wormhole structure, and the structural difference between HMS and MCM-41 is that the mesopores of HMS are arranged in disordered three dimensional wormlike arrays, whereas the mesopores of MCM-41 are arranged in a regular ordered arrays.

A heterometal can be introduced into a mesoporous substance either inside or outside the silica network. As an example of the method which is generally employed for introducing a heterometal into the silica network of a mesoporous substance, there can be mentioned a method in which a heterometal is added to the raw materials for the catalyst. As an example of the method which is generally employed for introducing a heterometal into the outside of the silica network, there can be mentioned an impregnation method.

The above-mentioned mesoporous substances are characterized in that the mesoporous substances comprise an amorphous silicon oxide having mesopores and having a very narrow pore diameter distribution. The method of the present invention can also be performed by using a catalyst comprising an amorphous silicon oxide which has mesopores but is not a mesoporous substance, namely a catalyst which does not exhibit a sharp pore diameter distribution in the meso range in a powder x-ray diffraction analysis. It is characteristic of the powder X-ray diffraction patterns of the mesoporous substance and the non-mesoporous substance having mesopores that the mesoporous substance exhibits a sharp peak at about 2 to 3 in terms of the 2θ/deg value, whereas the non-mesoporous substance having mesopores exhibits only a broad peak having low intensity. The difference of the method for producing a mesoporous substance from the method for producing a non-mesoporous substance is that, as mentioned above, the long aging time is needed for producing a mesoporous substance. Specifically, in the above-mentioned documents, the aging times necessary for producing MCM-41 and HMS are as long as 48 hours and 18 hours, respectively.

A catalyst comprising an amorphous silicon oxide which has mesopores but is not a mesoporous substance can be synthesized by a method in which a template which is similar to that used for producing a mesoporous substance is used but the aging time is shorter than used in the production of the mesoporous substance. Examples of silica sources include a silicon alkoxide, namely alkoxysilanes (e.g., tetraethoxysilane and tetramethoxysilane), slica gel and fumed silica. Among them, a silicon alkoxide is preferred.

A catalyst comprising a non-mesoporous amorphous silicon oxide having mesopores can be produced by adding a specific compound to the above-mentioned silica source. Examples of such specific compounds include surfactants, such as an anionic surfactant, a cationic surfactant and a nonionic surfactant; alkylamines and alkyldiamines. A quaternary ammonium salt which is a cationic surfactant is preferably used, but a quaternary ammonium salt having no activity or only low activity as a surfactant can also be used. Examples of quaternary ammonium salts which can be used for producing a catalyst comprising a non-mesoporous amorphous silicon oxide having mesopores include a hydroxide, bromide and chloride of tetramethylammonium, tetraethylammonium, tetrapropylammonium and terabutylammonium; and a hydroxide, bromide and chloride of a quaternary ammonium having a long chain alkyl group as one of its four alkyl groups, such as cetyl(hexadecyl)trimethylammonium, cetyltriethylammonium, cetyldimethylethylammonium and octyldecyltrimethylammonium.

Among these, cetyltrimethylammonium hydroxide is preferred. A template introduced into the catalyst can be removed by solvent extraction or by decomposition by calcination.

After mixing all of the raw materials for the catalyst with the above-mentioned template, the resultant mixture is agitated to thereby perform an aging of the mixture. The time needed for aging by agitation is only about 1 hour or less. After the aging, the resultant mixture is subjected to drying and calcination. Of course, the aging may be performed for more than 1 hour without causing any problems. Further, a heterometal may be introduced into the catalyst. The introduction of the heterometal can be performed by adding a heterometal to the Si source to thereby obtain a catalyst having the heterometal incorporated therein, or alternatively, by immersing a calcined catalyst into a solution or suspension containing a heterometal to thereby obtain a catalyst having the heterometal carried thereon.

In the present invention, the oxidation reaction can be performed in the gaseous or liquid phase using a fixed-bed or slurry-bed reactor. The reaction can be performed in a continuous or batchwise manner. When the oxidation reaction is performed in the liquid phase, the oxidation reaction can be performed in the presence of a solvent.

There is no particular limitation with respect to the solvent used in the present invention. Specific examples of such solvents include $C_1$–$C_{10}$ alcohols (such as methanol and t-butanol), acetonitrile, benzene, toluene, dimethylformamide, dimethyl sulfoxide, triethylamine, dimethoxyethane, dioxane, diglyme and water.

The reaction conditions are appropriately determined, taking into consideration the type of the oxidizing agent used, the type of the catalyst used and the like. In general, the reaction can be performed under a pressure of from atmospheric pressure to 10 MPa and at a temperature of from room temperature to 350° C.

The reaction of the present invention can be performed in either the liquid phase or gaseous phase, but it is generally performed in the gaseous phase. The reaction conditions for performing the reaction in the gaseous phase are as follows. The reaction pressure is in the range of from atmospheric pressure to 5 MPa. When the reaction is performed under reduced pressure, an apparatus for maintaining the reaction pressure at a reduced pressure becomes necessary, and when the reaction is performed under a pressure exceeding 5 MPa, a high reaction temperature becomes necessary for performing the reaction in the gaseous phase and the amount of by-products is likely to be increased. The reaction temperature for the method of the present invention is in the range of from 80° C. to 350° C. When the reaction temperature is lower than 80° C., it becomes difficult to perform the reaction in the gaseous phase, and when the reaction temperature is higher than 350° C., the amount of by-products is likely to be increased.

There is no particular limitation with respect to the oxidizing agent used in the present invention, as long as the oxidizing agent is stable and exhibits satisfactory vapor pressure under the reaction conditions employed. A preferred oxidizing agent is oxygen. Oxygen can be used in combination with nitrogen gas. Air can be also used as the oxygen source. In general, the molar ratio of oxygen to an alicyclic primary amine is in the range of from 0.1 to 20. When the molar ratio of oxygen is less than 0.1, the conversion of an alicyclic amine and the yield of the produced lactam are likely to become lowered. When the molar ratio of oxygen exceeds 20, the amount of by-products is likely to become increased and the yield of the produced lactam is likely to become lowered.

The amount of an amine contained in a feedstock gas is 1 to 20 vol %. The space velocity (SV) of the feedstock gas is 20 to 3000 hr$^{-1}$. Needless to say, appropriate conditions for maintaining the gaseous phase vary depending on the type of the raw material amine used and the type of the lactam produced and, therefore, the reaction pressure, the reaction temperature, the molar ratio of oxygen to the raw material amine and the SV value should be appropriately selected from the above-mentioned ranges so as to maintain the gaseous phase.

A lactam obtained by the oxidation reaction of an alicyclic primary amine is generally obtained in the form of a reaction mixture containing unreacted raw material amine and oxidation by-products. Accordingly, it is preferred that the method of the present invention further comprises a step for separating the produced lactam from a reaction system of the oxidation reaction. When the alicyclic primary amine is cyclohexylamine, the produced lactam is ε-caprolactam which is mainly used as a raw material for nylon 6 and, in general, is required to have a purity of not less than 99.9%. The obtained lactam can be separated from the reaction system by a customary method, such as distillation, extraction, crystal deposition, hydrogenation, ion exchange or treatment with activated carbon. These methods can be performed individually or in combination to thereby obtaining a lactam having a desired purity. When the oxidation reaction is performed in a gaseous phase and when both the conversion of the raw material amine and the selectivity for lactam are close to 100%, the produced lactam can be separated from the reaction system simply by removing the gas from the reaction system.

The alicyclic primary amine used in the method of the present invention is preferably a compound obtained by subjecting to an amination reaction at least one compound selected from the group consisting of an alicyclic alcohol and an alicyclic ketone. Further, in the present invention, it is preferred that at least a part of one or more by-products formed in the oxidation reaction of the alicyclic primary amine is recycled to a reaction system of the above-mentioned amination reaction.

The reaction products formed in the oxidation reaction of an alicyclic primary amine include not only lactam and unreacted raw material amine, but also a cycloalkanone oxime, an alicyclic alcohol, an alicyclic ketone, a condensate of an alicyclic alcohol and an alicyclic ketone, and the like. In general, the unreacted amine can be recycled to the reaction system of the oxidation reaction of an amine, and the cycloalkanone oxime can be converted into a lactam by a conventional method. Further, the alicyclic alcohol, the alicyclic ketone and the condensate thereof can be recycled to the reaction system of the amination reaction to convert these by-products into an alicyclic primary amine which can be used as a raw material, thereby increasing the yield of a lactam.

When the alicyclic primary amine used in the method of the present invention is cyclohexylamine and the produced lactam is ε-caprolactam, cyclohexanol and cyclohexanone are formed as the alicyclic alcohol and the alicyclic ketone, respectively, and these compounds can be recycled to the reaction system of the amination reaction.

In the method of the present invention, the amination reaction of at least one compound selected from the group consisting of an alicyclic alcohol and an alicyclic ketone can be performed by a conventional process.

For example, when at least one compound selected from the group consisting of cyclohexanol and cyclohexanone is used, the amination reaction thereof can be performed by any of the following conventional processes. Examples of conventional processes for performing the amination reaction of cyclohexanol include a process comprising reacting cyclohexanol with ammonia in a gaseous phase in the presence of hydrogen, using copper oxide/zinc oxide as a catalyst (see "Kougyoukagakuzasshi (Journal of the Society of Chemical Industry)", Vol. 70 (1967), No. 9, page 1508); a process comprising reacting cyclohexanol with ammonia in a gaseous phase in the presence of hydrogen, under atmospheric pressure using a reduced nickel-containing shaped catalyst, wherein the reduced nickel is supported on diatomaceous earth (see Examined Japanese Patent Application Publication No. Sho 51-41627); a process comprising reacting cyclohexanol with ammonia in a liquid phase at a high temperature in the presence of hydrogen under a high pressure using a catalyst comprised mainly of cobalt (see Examined Japanese Patent Application Publication No. Sho 51-32601); and a process comprising reacting cyclohexanol with ammonia in the presence of water, using a ruthenium-containing catalyst (see Unexamined Japanese Patent Application Laid-Open Specification No. Hei 6-1758).

Examples of conventional processes for performing the amination reaction of cyclohexanone include a process comprising reacting cyclohexanone with ammonia in a gaseous phase in the presence of hydrogen, using nickel, cobalt, platinum or paradium as a catalyst (see Chemical Abstract, 15, 1285, 1921); and process comprising reacting cyclohexanone with ammonia in a liquid phase in the presence of hydrogen, using nickel as a catalyst (see "Kougyoukagakuzasshi (Journal of the Society of Chemical Industry)", Vol. 70 (1967), No. 8, page 1335).

Examples of conventional processes for performing the amination reaction of a mixture of cyclohexanol and cyclohexanone include a process comprising reacting a mixture of cyclohexanol and cyclohexanone with ammonia in the presence of hydrogen, using a nickel oxide/chromium oxide catalyst (see French Patent No. 1,492,098); and a process comprising reacting a mixture of cyclohexanol and cyclohexanone with ammonia in a gaseous phase using a catalyst comprised of nickel and/or cobalt, and phosphoric acid or boric acid (see Examined Japanese Patent Application Publication No. Sho 41-7575).

The amination reaction can be performed in the presence of ammonia and hydrogen using a catalyst.

As the amination catalyst, there can be mentioned various metals, metal oxides, metal salts and organo-metal compounds. It is preferred that the amination catalyst comprises at least one metal selected from the group consisting of metals belonging to Groups 8, 9 and 10 of the Periodic Table (such as Fe, Co, Ni, Ru, Rh, Pd, Ir and Pt), Cr, Cu, Ag, Zn and Al. The amination catalyst may comprise a single metal, a plurality of metals, or a metal compound(s) (such as a metal oxide), and the catalyst may comprise a carrier having supported thereon any of the above-mentioned metals or metal compounds. Examples of carriers include an activated carbon, $SiO_2$, $Al_2O_3$, $SiO_2/Al_2O_3$, $TiO_2$, $ZrO_2$, $ZnO$, barium sulfate, potassium carbonate, diatomaceous earth and a zeolite.

The amination reaction can be performed in a gaseous or liquid phase using a fixed-bed, slurry-bed or fluidized-bed reactor. The reaction can be performed in a continuous or batchwise manner.

When the reaction is performed in a liquid phase, a solvent can be used. With respect to the solvent, there is no particular limitation. Examples of solvents include nitriles, such as acetonitrile and propionitrile; aliphatic hydrocarbons, such as n-hexane and cyclohexane; aromatic compounds, such as benzene and toluene; ethers, such as dioxane and diglyme; and water. When the amination reaction is performed in the presence of a solvent, the amount of cyclohexanol is generally from 1 to 30% by weight, preferably from 3 to 20% by weight, based on the total weight of the alicyclic alcohol and the solvent. The solvent can also be used when the amination reaction is performed in a gaseous phase. In this case, the solvent can be introduced in a gaseous form into the reactor.

The amination reaction can be performed using a catalyst which has been pretreated with hydrogen. The use of a hydrogen-pretreated catalyst in the amination reaction is effective not only in that the catalytic activity of the catalyst can be maintained for a long period of time, but also in that the selectivity for and yield of an alicyclic primary amine can be improved. The hydrogen-pretreatment of the catalyst can be performed by heating the catalyst in the presence of hydrogen in the absence of a main raw material (i.e., alicyclic alcohol and/or an alicyclic ketone) and in the absence or presence of a solvent. The heating is generally performed at a temperature in the range of from 100 to 500° C. The hydrogen-pretreatment can be performed in a batchwise manner using an agitation reactor or in a continuous manner using a tubular reactor.

In the amination reaction, the molar ratio of at least one compound selected from the group consisting of an alicyclic alcohol and an alicyclic ketone:ammonia:water is generally from 1:1:1 to 1:10:10. The reaction conditions can be appropriately determined, taking into consideration the type of the reaction system, the type of the catalyst used and the like. The reaction pressure is generally from 0.1 to 10 MPa and the reaction temperature is generally from 80 to 250° C.

The alicyclic primary amine produced by the amination reaction is recovered from the reaction mixture in the reactor by any customary methods, such as distillation and extraction, and if desired, the alicyclic primary amine is further subjected to treatment for isolation, thereby obtaining an alicyclic primary amine having a desired purity. In general, it is preferred that the alicyclic alcohol (or an alicyclic ketone or a mixture thereof) which remains unreacted and the ammonia which remains unreacted (each of which is recovered from the reactor) can be recycled to the reactor of the amination reaction system.

BEST Mode for Carrying Out the Invention

Hereinbelow, the present invention will be described in more detail with reference to the following Examples and Comparative Examples, which should not be construed as limiting the scope of the present invention.

In the following Examples and Comparative Examples, various measurements were conducted using the following apparatuses.

Gas Chromatography (GC) Apparatus:
  Gas chromatograph Model GC-14B (manufactured and sold by Shimadzu Corporation, Japan)

GC Column:
  DB-1701 (manufactured and sold by J & W Scientific, U.S.A.)

Conditions for GC:
  Injection temperature: 250° C.
  Column temperature: Initially, the temperature was maintained at 50° C. and, then, the temperature was elevated at a rate of 10° C./min to 250° C.

Powder X-Ray Diffraction Measuring Apparatus:
  RAD-IIIA (manufactured and sold by Rigaku Corporation, Japan)

Energy Dispersive X-Ray Analysis System:
  EMAX-5770W (manufactured and sold by Horiba Ltd., Japan)

Pore Size Distribution Measuring Apparatus:
  Autosorb-3 MP (manufactured and sold by Quantachrome Instruments, U.S.A.)

EXAMPLE 1

<Catalyst: $SiO_2$ (1)>
To 71 g of tetraethoxysilane ($Si(OC_2H_5)_4$; manufactured and sold by Wako Pure Chemical Industries, Ltd., Japan) was added 125 g of water, and thereto was further added 10 ml of a 28% by weight aqueous ammonia while stirring. After adding 10 ml of ethanol to the resultant mixture, the stirring of the mixture was continued for 1 hour. Using a rotary evaporator, the mixture was heated to dryness under reduced pressure in an oil bath at 120° C., thereby obtaining a dried product. The obtained dried product was subjected to further drying in an electric kiln at 120° C. for 12 hours, followed by calcination at 400° C. for 4 hours, thereby obtaining a solid catalyst. The catalyst was subjected to a powder X-ray diffraction analysis as described above. The results of the X-ray diffraction analysis showed that the catalyst was an amorphous silicon oxide.

The above-obtained catalyst was charged into a reaction vessel (outer diameter: 12.7 mm, inner diameter: 9.0 mm, length: 100 mm) which was made of SUS316 and which was provided with conduits for introducing cyclohexylamine and molecular oxygen, respectively; a sheath tube for inserting a thermocouple therein, wherein the thermocouple was used to measure the temperature of a catalyst layer formed inside the reaction vessel; and a layer of SUS316 fillers for vaporizing cyclohexylamine. Then, the reaction vessel containing the catalyst was placed in a heating furnace. To the reaction vessel was attached a line for withdrawing a part of a gaseous reaction mixture from an outlet of the reaction vessel and introducing the withdrawn reaction mixture into the GC apparatus, while maintaining the gaseous state of the reaction mixture. The gaseous reaction mixture introduced into the GC apparatus through the above-mentioned line was analyzed under the above-mentioned conditions. The conversion of cyclohexylamine and selectivity for ε-caprolactam were calculated from the results of the GC analysis.

After purging the reaction vessel with nitrogen gas, the reaction vessel was heated to and maintained at 160° C. The reaction was started by feeding cyclohexylamine and oxygen into the reaction vessel. The feeding of cyclohexylamine and oxygen was performed under conditions wherein the composition of the mixture of cyclohexylamine, oxygen and nitrogen around the inlet of the reaction vessel became: cyclohexylamine=5.1% by volume, oxygen=6.6% by volume, and nitrogen=88.3% by volume, and wherein the SV value became 270 to 380 $h^{-1}$. 20 Hours after the start of the reaction, the temperature of the reaction vessel was elevated to 180° C. 25 Hours after the start of the reaction, the conversion of cyclohexylamine was 17% and the selectivity for ε-caprolactam was 3%.

COMPARATIVE EXAMPLE 1

<Catalyst: Al₂O₃>

A reaction was performed in substantially the same manner as in Example 1, except that alumina (high purity alumina NRK-301, manufactured and sold by Nishio Industries, Japan) was used as the solid catalyst, the reaction was started at 160° C., the temperature of the reaction vessel was elevated to 180° C. at the point in time of 30 hours after the start of the reaction, further elevated to 200° C. at the point in time of 45 hours after the start of the reaction, and further elevated to 230° C. at the point in time of 49 hours after the start of the reaction. No ε-caprolactam was produced throughout the reaction.

EXAMPLE 2

<Catalyst: SiO₂ (2)>

To 71 g of tetraethoxysilane was added 125 g of water, and thereto was further added 0.1371 g of ammonium sulfate while stirring, followed by addition of 12.5 ml of a 28% by weight aqueous ammonia. After adding 10 ml of ethanol to the resultant mixture, the stirring of the mixture was continued for 1 hour. Using a rotary evaporator, the mixture was heated to dryness under reduced pressure in an oil bath to thereby obtain a dried product, wherein the temperature of the oil bath was initially maintained at 60° C. and elevated to 120° C. The obtained dried product was subjected to further drying in an electric kiln at 120° C. for 12 hours, followed by calcination at 400° C. for 4 hours, thereby obtaining a solid catalyst. The catalyst was subjected to a powder X-ray diffraction analysis as described above. The results of the X-ray diffraction analysis showed that the catalyst was an amorphous silicon oxide.

A reaction was performed in substantially the same manner as in Example 1, except that the above-obtained catalyst was used as the solid catalyst and the temperature of the reaction vessel was maintained at 160° C. 21 Hours after the start of the reaction, the conversion of cyclohexylamine was 21% and the selectivity for ε-caprolactam was 2%.

EXAMPLE 3

<Catalyst: SiO₂ (2)>

A reaction was performed in substantially the same manner as in Example 2, except that the temperature of the reaction vessel was maintained at 180° C. 8 Hours after the start of the reaction, the conversion of cyclohexylamine was 32% and the selectivity for ε-caprolactam was 5%.

EXAMPLE 4

<Catalyst: V₂O₅/SiO₂>

To 0.383 g of ammonium metavanadate (NH₄VO₃; manufactured and sold by Wako Pure Chemical Industries, Ltd., Japan) were added 9.2 g of water and 26.5 g of a 10% by weight aqueous solution of tetrapropylammonium hydroxide ([(CH₃CH₂CH₂)₄N]OH; manufactured and sold by Wako Pure Chemical Industries, Ltd., Japan), followed by stirring, and thereto was further added 17.33 g of tetraethoxysilane while stirring (Si/V atomic ratio=25). The stirring of the resultant mixture was continued at room temperature for 5 hours. Using a rotary evaporator, the mixture was heated to dryness under reduced pressure in an oil bath to thereby obtain a dried product, wherein the temperature of the oil bath was initially maintained at 60° C. and elevated to 120° C. The obtained dried product was subjected to calcination at 550° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, and the temperature of the reaction vessel was maintained at 160° C. 28 Hours after the start of the reaction, the conversion of cyclohexylamine was 2% and the selectivity for ε-caprolactam was 3%.

EXAMPLE 5

<Catalyst: MoO₃/SiO₂>

To 0.57 g of molybdenum trioxide (MoO₃; manufactured and sold by Wako Pure Chemical Industries, Ltd., Japan) were added 9.2 g of water and 26.5 g of a 10% by weight aqueous tetrapropylammonium hydroxide solution, followed by stirring, and thereto was further added 17.33 g of tetraethoxysilane while stirring (Si/Mo atomic ratio=21). The stirring of the resultant mixture was continued at room temperature for 5 hours. Using a rotary evaporator, the mixture was heated to dryness under reduced pressure in an oil bath to thereby obtain a dried product, wherein the temperature of the oil bath was initially maintained at 60° C. and elevated to 120° C. The obtained dried product was subjected to calcination at 550° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 160° C., the temperature of the reaction vessel was elevated to 180° C. at the point in time of 19 hours after the start of the reaction, and further elevated to 200° C. at the point in time of 28 hours after the start of the reaction. 6 Hours after the start of the reaction, the conversion of cyclohexylamine was 3% and the selectivity for ε-caprolactam was 1%; 26 hours after the start of the reaction, the conversion of cyclohexylamine was 5% and the selectivity for ε-caprolactam was 2%; and 42 hours after the start of the reaction, the conversion of cyclohexylamine was 15% and the selectivity for ε-caprolactam was 5%.

EXAMPLE 6

<Catalyst: TiO₂/SiO₂>

To 17.75 g of tetraethoxysilane were added 2.0 g of methanol and 31.3 g of water while stirring, and thereto was further added 3.5532 g of titanium tetra-isopropoxide (Ti[OCH(CH₃)₂]₄; manufactured and sold by Wako Pure Chemical Industries, Ltd., Japan) (Si/Ti atomic ratio=6). After adding 2.5 g of a 28% aqueous ammonia, the stirring of the mixture was continued at room temperature for 1 hour. Using a rotary evaporator, the mixture was heated to dryness under reduced pressure in an oil bath to thereby obtain a dried product, wherein the temperature of the oil bath was initially maintained at 60° C. and elevated to 120° C. The obtained dried product was subjected to calcination at 400° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 160° C., the temperature of the reaction vessel was elevated to 180° C. at the point in time of 19 hours after the start of the reaction, and further elevated to 200° C. at the point in time of 28 hours after the start of the reaction. 12 Hours after the start of the reaction, the conversion of cyclohexylamine was 8% and the selectivity for $\epsilon$-caprolactam was 5%; 23 hours after the start of the reaction, the conversion of cyclohexylamine was 8% and the selectivity for $\epsilon$-caprolactam was 7%; and 31 hour after the start of the reaction, the conversion of cyclohexylamine was 9% and the selectivity for $\epsilon$-caprolactam was 15%.

EXAMPLE 7

<Catalyst: $Al_2O_3/SiO_2$ (1)>

To 15 g of tetraethoxysilane was added 10.0 g of aluminum sec-butoxide ($Al[O(CH_3)CH(C_2H_5)]3$; manufactured and sold by Sigma-Aldrich Co., U.S.A) (Si/Al atomic ratio=1.8), followed by stirring, and thereto was further added 6.3 g of water while stirring. The stirring of the resultant mixture was continued at room temperature for 1 hour. Using a rotary evaporator, the mixture was heated to dryness under reduced pressure in an oil bath at 120° C., thereby obtaining a dried product. The obtained dried product was subjected to calcination at 200° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 160° C., and the temperature of the reaction vessel was elevated to 180° C. at the point in time of 32 hours after the start of the reaction. 48 Hours after the start of the reaction, the conversion of cyclohexylamine was 15% and the selectivity for $\epsilon$-caprolactam was 5%.

EXAMPLE 8

<Catalyst: $Al_2O_3/SiO_2$ (2)>

To 180 g of tetraethoxysilane was added 6.0 g of aluminum sec-butoxide (Si/Al atomic ratio=35.5), and thereto was added 46.5 g of water while stirring. The resultant mixture was stirred at room temperature for 1 hour. Using a rotary evaporator, the mixture was heated to dryness under reduced pressure in an oil bath to thereby obtain a dried product, wherein the temperature of the oil bath was initially maintained at 80° C. and elevated to 120° C. The obtained dried product was subjected to calcination at 200° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 160° C., the temperature of the reaction vessel was elevated to 180° C. at the point in time of 21 hours after the start of the reaction, and further elevated to 200° C. at the point in time of 31 hours after the start of the reaction. 20 Hours after the start of the reaction, the conversion of cyclohexylamine was 3% and the selectivity for $\epsilon$-caprolactam was 13%; 25 hours after the start of the reaction, the conversion of cyclohexylamine was 3% and the selectivity for $\epsilon$-caprolactam was 28%; and 33 hours after the start of the reaction, the conversion of cyclohexylamine was 3% and the selectivity for $\epsilon$-caprolactam was 42%.

EXAMPLE 9

<Catalyst: $Al_2O_3/SiO_2$ (3)>

To 120 g of tetraethoxysilane was added 2.4 g of aluminum sec-butoxide (Si/Al atomic ratio=58.2), and thereto was further added 31 g of water while stirring. The resultant mixture was stirred at room temperature for 1 hour. Using a rotary evaporator, the mixture was heated to dryness under reduced pressure in an oil bath to thereby obtain a dried product, wherein the temperature of the oil bath was initially maintained at 70° C. and elevated to 120° C. The obtained dried product was subjected to calcination at 200° C. for 4 hours, thereby obtaining a solid catalyst. The catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 160° C., the temperature of the reaction vessel was elevated to 180° C. at the point in time of 12 hours after the start of the reaction, and further elevated to 200° C. at the point in time of 20 hours after the start of the reaction. 19 Hours after the start of the reaction, the conversion of cyclohexylamine was 2% and the selectivity for $\epsilon$-caprolactam was 7%; and 24 hours after the start of the reaction, the conversion of cyclohexylamine was 3% and the selectivity for $\epsilon$-caprolactam was 15%.

EXAMPLE 10

<Catalyst: $Al_2O_3/SiO_2$ (4)>

A catalyst was prepared in substantially the same manner as in Example 8, except that the calcination of the dried product was performed at 300° C. for 4 hours to obtain a solid catalyst. The obtained catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 200° C., the temperature of the reaction vessel was once lowered to 180° C. at the point in time of 15 hours after the start of the reaction and, then, elevated to 220° C. at the point in time of 24 hours after the start of the reaction. 4 Hours after the start of the reaction, the conversion of cyclohexylamine was 2% and the selectivity for $\epsilon$-caprolactam was 6%; and 24 hours after the start of the reaction, the conversion of cyclohexylamine was 1% and the selectivity for $\epsilon$-caprolactam was 5%.

EXAMPLE 11

<Catalyst: $Al_2O_3/SiO_2$ (5)>

A catalyst was prepared in substantially the same manner as in Example 8, except that the calcination of the dried product was performed at 400° C. for 4 hours to obtain a solid catalyst. The obtained catalyst was subjected to a powder X-ray diffraction analysis as described above. The results of the X-ray diffraction analysis showed that the catalyst was comprised of an amorphous silica.

A reaction was performed in substantially the same manner as in Example 1, except that the obtained catalyst was used as the solid catalyst, the reaction was started at 200° C., and the temperature of the reaction vessel was once lowered to 180° C. at the point in time of 15 hours after the start of the reaction and, then, elevated to 220° C. at the point in time of 24 hours after the start of the reaction. 7 Hours after the start of the reaction, the conversion of cyclohexylamine was 2% and the selectivity for ε-caprolactam was 6%; and 29 hours after the start of the reaction, the conversion of cyclohexylamine was 1% and the selectivity for ε-caprolactam was 6%.

EXAMPLE 12

<Catalyst: $Al_2O_3/SiO_2$ (6)>

To 4.13 g of aluminum sec-butoxide were added 121.3 g of a 10% by weight aqueous tetrapropylammonium hydroxide solution and 170 g of water, followed by stirring. Thereto was further added 104 g of tetraethoxysilane (Si/Al atomic ratio=30) while stirring. The resultant mixture was heated to and maintained at 60° C. and stirred at this temperature for 30 minutes. Subsequently, the heated mixture was allowed to stand still at room temperature for 1 hour. Using a rotary evaporator, the mixture was heated to dryness under reduced pressure in an oil bath to thereby obtain a dried product, wherein the temperature of the oil bath was initially maintained at 60° C. and elevated to 120° C. The obtained dried product was subjected to calcination at 550° C. for 5 hours, followed by further calcination at 600° C. for 1 hour, thereby obtaining a solid catalyst. The catalyst was subjected to a powder X-ray diffraction analysis as described above. The results of the X-ray diffraction analysis showed that the catalyst was comprised of an amorphous silica. In the X-ray diffraction pattern, the amorphous silica exhibited a broad peak at around 2 in terms of the 2θ/deg value, and this result revealed that the amorphous silica had mesopores. The measurement of the pore size distribution of the catalyst also showed that the amorphous silica contained in the catalyst had mesopores (namely pores having a pore diameter about 3 nm) as well as macropores.

A reaction was performed in substantially the same manner as in Example 1, except that the obtained catalyst was used as the solid catalyst, and the temperature of the reaction vessel was maintained at 195° C. 5 Hours after the start of the reaction, the conversion of cyclohexylamine was 15% and the selectivity for ε-caprolactam was 36%.

EXAMPLE 13

<Catalyst: $Al_2O_3/SiO_2$ (6)>

A reaction was performed in substantially the same manner as in Example 1, except that the catalyst obtained in Example 12 was used as the solid catalyst, and the temperature of the reaction vessel was maintained at 215° C. 6 Hours after the start of the reaction, the conversion of cyclohexylamine was 14% and the selectivity for ε-caprolactam was 36%.

EXAMPLE 14

<Catalyst: $Al_2O_3/SiO_2$ (7)>

To 120 g of tetraethoxysilane was added 0.27 g of aluminum isopropoxide ($Al[OCH(CH_3)_2]_3$; manufactured and sold by Wako Pure Chemical Industries, Ltd., Japan) while stirring (Si/Al atomic ratio=436), thereby obtaining an alkoxide mixture solution. The obtained alkoxide mixture solution was added to a solution containing 9 g of hexadecyltrimethylammonium bromide and 16.65 ml of a 20% hydrochloric acid. The resultant mixture was stirred at room temperature for 1 hour.

A 10% aqueous ammonia was dropwise added to the resultant mixture so as to obtain a mixture having a pH of 5. The thus obtained mixture was dried at 70 to 80° C. for 4 hours, followed by further drying at 400° C. for 4 hours, thereby obtaining a dried product. The dried product was subjected to calcination at 550° C. for 10 hours, thereby obtaining a solid catalyst. The catalyst was subjected to a powder X-ray diffraction analysis as described above. The results of the X-ray diffraction analysis showed that the catalyst was comprised of an amorphous silica. In the X-ray diffraction pattern, the amorphous silica exhibited a broad peak at around 2 to 3 in terms of the 2θ/deg value. Further, the measurement of the pore size distribution of the catalyst showed that the amorphous silica contained in the catalyst had a wide pore diameter distribution wherein the pore diameter ranged from 2 to 15 nm.

A reaction was performed in substantially the same manner as in Example 1, except that the obtained catalyst was used as the solid catalyst, and the temperature of the reaction vessel was maintained at 215° C. 4 Hours after the start of the reaction, the conversion of cyclohexylamine was 41% and the selectivity for ε-caprolactam was 18%.

EXAMPLE 15

<Catalyst: $Al_2O_3/SiO_2$ (8)>

A catalyst was prepared in substantially the same manner as in Example 14, except that 0.55 g of aluminum isopropoxide (Si/Al atomic ratio=214) was used. The catalyst was subjected to a powder X-ray diffraction analysis as described above. The results of the X-ray diffraction analysis showed that the catalyst was comprised of an amorphous silica. In the X-ray diffraction pattern, the amorphous silica exhibited a broad peak at around 2 to 3 in terms of the 2θ/deg value. Further, the measurement of the pore size distribution of the catalyst showed that the amorphous silica contained in the catalyst had a wide pore diameter distribution wherein the pore diameter ranged from 2 to 15 nm.

A reaction was performed in substantially the same manner as in Example 1, except that the obtained catalyst was used as the solid catalyst, and the temperature of the reaction vessel was maintained at 215° C. 7 Hours after the start of the reaction, the conversion of cyclohexylamine was 40% and the selectivity for ε-caprolactam was 28%.

EXAMPLE 16

<Catalyst: $Al_2O_3/SiO_2$ (9)>

A catalyst was prepared in substantially the same manner as in Example 14, except that 1.32 g of aluminum isopropoxide (Si/Al atomic ratio=89) was used. The prepared catalyst was subjected to a powder X-ray diffraction analysis as described above. The results of the X-ray diffraction analysis showed that the catalyst was comprised of an amorphous silica. In the X-ray diffraction pattern, the amorphous silica exhibited a broad peak at around 2 to 3 in terms of the 2θ/deg value. Further, the measurement of the pore size distribution of the catalyst showed that the amorphous silica contained in the catalyst had a wide pore diameter distribution wherein the pore diameter ranged from 2 to 15 nm.

A reaction was performed in substantially the same manner as in Example 1, except that the obtained catalyst was used as the solid catalyst, and the temperature of the reaction vessel was maintained at 215° C. 7 Hours after the start of the reaction, the conversion of cyclohexylamine was 41% and the selectivity for ε-caprolactam was 26%.

EXAMPLE 17

<Catalyst: $Al_2O_3/SiO_2$ (8)>

A reaction was performed in substantially the same manner as in Example 1, except that the catalyst obtained in Example 14 was used as the solid catalyst, and the temperature of the reaction vessel was maintained at 160° C. 18 Hours after the start of the reaction, the conversion of cyclohexylamine was 19% and the selectivity for ε-caprolactam was 3%.

EXAMPLE 18

<Catalyst: MCM-41 (1) (Mesoporous Substance)>

To 21.8 g of a 15% aqueous solution of tetramethylammonium hydroxide (($CH_3)_4NOH$; manufactured and sold by Wako Pure Chemical Industries, Ltd., Japan) were added 0.48 g of a 85% sodium hydroxide reagent and 15.4 g of cetyltrimethylammonium bromide [$CH_3(CH_2)_{15}N(CH_3)_3$]Br; manufactured and sold by Wako Pure Chemical Industries, Ltd., Japan), thereby obtaining solution A. On the other hand, 11.14 g of tetraethoxysilane was mixed with 100 g of water, thereby obtaining solution B. Solution B was dropwise added to solution A while stirring solution A. The resultant mixture was stirred for 1 hour. Subsequently, the mixture was transferred to an autoclave, followed by hydrothermal synthesis at 100° C. for 2 days, to thereby obtain a slurry. The obtained slurry was subjected to filtration, and the resultant filtration residue was washed with an ion exchanged water, followed by drying at 110° C. for 5 hours, to thereby obtain a dried product. The obtained dried product was subjected to calcination at 550° C. for 8 hours, thereby obtaining a solid catalyst.

The obtained catalyst was subjected to a powder X-ray diffraction analysis as described above. In the X-ray diffraction pattern, a peak ascribed to mesopores was observed at 2 in terms of the 2θ/deg value, and this diffraction pattern was the same as that of MCM-41. The pore size distribution of the catalyst was measured as mentioned above. A sharp peak was observed in the pore diameter range of from 2 nm to 3 nm, and it was confirmed that the catalyst was MCM-41.

A reaction was performed in substantially the same manner as in Example 1, except that the obtained catalyst was used as the solid catalyst, the reaction was started at 160° C., the temperature of the reaction vessel was elevated to 170° C. at the point in time of 22 hours after the start of the reaction, and further elevated to 180° C. at the point in time of 28 hours after the start of the reaction. 16 Hours after the start of the reaction, the conversion of cyclohexylamine was 17% and the selectivity for ε-caprolactam was 9%; and 36 hours after the start of the reaction, the conversion of cyclohexylamine was 9% and the selectivity for ε-caprolactam was 9%.

EXAMPLE 19

<Catalyst: MCM-41 (2) (Mesoporous Substance)>

A catalyst was prepared in substantially the same manner as in Example 18, except that the hydrothermal synthesis was conducted for 3 days. The results of the powder X-ray diffraction analysis and the pore size distribution measurement confirmed that the catalyst was MCM-41.

A reaction was performed in substantially the same manner as in Example 1, except that the obtained catalyst was used as the solid catalyst, the reaction was started at 160° C., the temperature of the reaction vessel was elevated to 180° C. at the point in time of 22 hours after the start of the reaction, further elevated to 200° C. at the point in time of 32 hours after the start of the reaction, and further elevated to 220° C. at the point in time of 48 hours after the start of the reaction. 17 Hours after the start of the reaction, the conversion of cyclohexylamine was 13% and the selectivity for ε-caprolactam was 6%; 25 hours after the start of the reaction, the conversion of cyclohexylamine was 22% and the selectivity for ε-caprolactam was 8%; 39 hours after the start of the reaction, the conversion of cyclohexylamine was 12% and the selectivity for ε-caprolactam was 14%; and 53 hours after the start of the reaction, the conversion of cyclohexylamine was 14% and the selectivity for ε-caprolactam was 14%.

EXAMPLE 20

<Catalyst: W-MCM-41 (1) (Mesoporous Substance)>

To 21.9 g of a 15% aqueous tetramethylammonium hydroxide solution were added 0.48 g of a 85% sodium hydroxide reagent and 15.4 g of cetyltrimethylammonium bromide, thereby obtaining solution A. On the other hand, 0.1448 g of ammonium metatungstate (($NH_4)_6W_{12}O_{39}$; manufactured and sold by Sigma-Aldrich Co., U.S.A.) was dissolved in 100 g of water, and thereto was added 11.14 g of tetraethoxysilane (Si/W atomic ratio=90), thereby obtaining solution B. Solution B was dropwise added to solution A while stirring solution A.

The resultant mixture was stirred for 1 hour. Subsequently, the mixture was transferred to an auto-clave, followed by hydrothermal synthesis at 100° C. for 2 days, to thereby obtain a slurry. The obtained slurry was subjected to filtration, and the resultant filtration residue was washed with an ion exchanged water, followed by drying at 110° C. for 5 hours, to thereby obtain a dried product. The obtained dried product was subjected to calcination at 550° C. for 8 hours, thereby obtaining a solid catalyst. The results of the powder X-ray diffraction analysis and the pore size distribution measurement confirmed that the catalyst was MCM-41.

A reaction was performed in substantially the same manner as in Example 1, except that the obtained catalyst was used as the solid catalyst, the reaction was started at 160° C., the temperature of the reaction vessel was elevated to 180° C. at the point in time of 19 hours after the start of the reaction, and further elevated to 200° C. at the point in time of 28 hours after the start of the reaction. 16 Hours after the start of the reaction, the conversion of cyclohexylamine was 7% and the selectivity for ε-caprolactam was 5%; 22 hours after the start of the reaction, the conversion of cyclohexylamine was 8% and the selectivity for ε-caprolactam was 8%; and 29 hours after the start of the reaction, the conversion of cyclohexylamine was 11% and the selectivity for ε-caprolactam was 22%.

EXAMPLE 21

<Catalyst: W-MCM-41 (2) (Mesoporous Substance)>

A catalyst was prepared in substantially the same manner as in Example 20, except that 0.0724 g of ammonium metatungstate was used for preparing solution B (Si/W atomic ratio=181). The results of the powder X-ray diffraction analysis and the pore size distribution measurement confirmed that the catalyst was MCM-41.

A reaction was performed in substantially the same manner as in Example 1, except that the obtained catalyst was used as the solid catalyst, the reaction was started at 160° C., and the temperature of the reaction vessel was elevated to 180° C. at the point in time of 22 hours after the start of the reaction, and further elevated to 200° C. at the point in time of 32 hours after the start of the reaction. 16 Hours after the start of the reaction, the conversion of cyclohexylamine was 23% and the selectivity for ε-caprolactam was 8%; 26 hours after the start of the reaction, the conversion of cyclohexylamine was 25% and the selectivity for ε-caprolactam was 10%; and 34 hours after the start of the reaction, the conversion of cyclohexylamine was 30% and the selectivity for ε-caprolactam was 17%.

EXAMPLE 22

<Catalyst: W-MCM-41 (3) (Mesoporous Substance)>

A catalyst was prepared in substantially the same manner as in Example 20, except that 0.0362 g of ammonium metatungstate was used for preparing solution B (Si/W atomic ratio=362). The results of the powder X-ray diffraction analysis and the pore size distribution measurement confirmed that the catalyst was MCM-41.

A reaction was performed in substantially the same manner as in Example 1, except that the obtained catalyst was used as the solid catalyst, the reaction was started at 160° C., the temperature of the reaction vessel was elevated to 170° C. at the point in time of 23 hours after the start of the reaction, and further elevated to 180° C. at the point in time of 29 hours after the start of the reaction. 41 Hours after the start of the reaction, the conversion of cyclohexylamine was 18% and the selectivity for ε-caprolactam was 14%.

EXAMPLE 23

<Catalyst: W-MCM-41 (4) (Mesoporous Substance)>

A catalyst was prepared in substantially the same manner as in Example 20, except that 0.0270 g of ammonium metatungstate was used for preparing solution B (Si/W atomic ratio=485). The results of the powder X-ray diffraction analysis and the pore size distribution measurement confirmed that the catalyst was MCM-41.

A reaction was performed in substantially the same manner as in Example 1, except that the obtained catalyst was used as the solid catalyst, the reaction was started at 160° C., the temperature was elevated to 180° C. at the point in time of 12 hours after the start of the reaction, and further elevated to 200° C. at the point in time of 21 hour after the start of the reaction. 41 Hours after the start of the reaction, the conversion of cyclohexylamine was 18% and the selectivity for ε-caprolactam was 14%; 20 hours after the start of the reaction, the conversion of cyclohexylamine was 11% and the selectivity for ε-caprolactam was 8.%; and 26 hours after the start of the reaction, the conversion of cyclohexylamine was 13% and the selectivity for ε-caprolactam was 15%.

EXAMPLE 24

<Catalyst: Al-HMS (1) (Mesoporous Substance)>

"HMS" is an abbreviation for hexagonal mesoporous silica. HMS is known to have an irregular and disordered structure and it is clearly distinct from MCM-41. In this Example, HMS was prepared as follows. To 50 g of water were added 160 g of ethanol and 20 g of dodecylamine ($CH_3(CH_2)_{11}NH_2$; manufactured and sold by Wako Pure Chemical Industries, Ltd., Japan) in this order, thereby obtaining a solution. 83 g of tetraethoxysilane was dropwise added to the obtained solution while stirring. Thereto was further added an aluminum isopropoxide solution obtained by dissolving 3.27 g of aluminum isopropoxide in 10 g of isopropanol (Si/Al atomic ratio=30), wherein the aluminum isopropoxide solution was dropwise added to the above-obtained mixture while stirring. The resultant mixture was stirred at room temperature for 30 minutes and, then, allowed to stand still at room temperature for 20 hours, thereby obtaining a slurry.

The above-obtained slurry was subjected to filtration, and the resultant filtration residue was washed with an ion exchanged water, followed by drying at 115° C. for 5 hours, to thereby obtain a dried product. The obtained dried product was washed with ethanol to thereby remove most of the residual dodecylamine. Subsequently, the washed product was subjected to calcination in an electric kiln at 300° C. for 2 hours and, then, the temperature was elevated at a rate of 1° C./min to 550° C. and maintained at 550° C. for 4 hours, thereby obtaining a solid catalyst.

The obtained catalyst was subjected to a powder X-ray diffraction analysis as described above. In the X-ray diffraction pattern, a peak ascribed to mesopores was observed at around 2 in terms of the 2θ/deg value. Further, the pore size distribution of the catalyst was measured as mentioned above. A sharp peak was observed in the pore diameter range of from 3 nm to 4 nm, and it was confirmed that the obtained catalyst was HMS.

A reaction was performed in substantially the same manner as in Example 1, except that the obtained catalyst was used as the solid catalyst, and the temperature of the reaction vessel was maintained at 190° C. 8 Hours after the start of the reaction, the conversion of cyclohexylamine was 35% and the selectivity for ε-caprolactam was 11%.

EXAMPLE 25

<Catalyst: Al-HMS (2) (Mesoporous Substance)>

A catalyst was prepared in substantially the same manner as in Example 24, except that 1.98 g of aluminum isopropoxide (Si/Al atomic ratio=50) was used. The results of the powder X-ray diffraction analysis and the pore size distribution measurement confirmed that the catalyst was HMS.

A reaction was performed in substantially the same manner as in Example 1, except that the obtained catalyst was used as the solid catalyst, and the temperature of the reaction vessel was maintained at 190° C. 9 Hours after the start of the reaction, the conversion of cyclohexylamine was 33% and the selectivity for ε-caprolactam was 17%.

EXAMPLE 26

<Catalyst: Al-HMS (3) (Mesoporous Substance)>

A catalyst was prepared in substantially the same manner as in Example 24, except that 1.40 g of aluminum isopropoxide (Si/Al atomic ratio=70) was used. The results of the powder X-ray diffraction analysis and the pore size distribution measurement confirmed that the catalyst was HMS.

A reaction was performed in substantially the same manner as in Example 1, except that the obtained catalyst was used as the solid catalyst, and the temperature of the reaction vessel was maintained at 190° C. 7 Hours after the start of the reaction, the conversion of cyclohexylamine was 33% and the selectivity for ε-caprolactam was 7%.

EXAMPLE 27

<Catalyst: SAPO-11 (Phosphate Zeolite)>

276.0 g of water and 88.5 g of a 85% by weight aqueous phosphate solution were mixed together, and thereto was added 156.5 g of aluminum isopropoxide, followed by stirring. 3.1 g of powdery silica was added to the mixture, followed by stirring, thereby obtaining a homogenous mixture. Thereto was further added 49.1 g of di-n-propylamine (($CH_3CH_2CH_2$)$_2$NH; manufactured and sold by Wako Pure Chemical Industries, Ltd., Japan) and further stirred until a homogeneous mixture was obtained. The thus obtained homogeneous mixture was transferred to a 1-liter autoclave, followed by hydrothermal synthesis at 150° C. for 133 hours, thereby obtaining a slurry. The obtained slurry was subjected to filtration, and the resultant filtration residue was washed with an ion exchanged water, followed by drying, thereby obtaining a dried product. The dried product was calcined in air at 500° C. for 2 hours, thereby obtaining a calcined, crystalline powder.

The obtained crystalline powder was subjected to a powder X-ray diffraction analysis as described above. From the X-ray diffraction pattern, the crystalline powder was confirmed to be silicoaluminophophate SAPO-11. The crystalline powder was further subjected to an energy dispersive X-ray analysis. As a result, it was found that the ($P_2O_5+Al_2O_3$)/$SiO_2$ molar ratio of the crystalline powder was 7.8.

The calcined, crystalline powder (SAPO-11) was added to a 1 N aqueous ammonium nitrate solution to thereby obtain a 10% by weight SAPO-11 slurry, and the obtained slurry was subjected to an ion exchange treatment at room temperature for 3 hours. The resultant slurry was subjected to filtration, and the resultant filtration residue was washed with an ion exchanged water, followed by drying at 120° C. for 10 hours, to thereby obtain a dried product. The obtained dried product was subjected to calcination at 530° C. for 3 hours, thereby obtaining an H-type SAPO-11 catalyst.

A reaction was performed in substantially the same manner as in Example 1, except that the obtained catalyst was used as the solid catalyst, the reaction was started at 160° C., the temperature of the reaction vessel was elevated to 180° C. at the point in time of 24 hours after the start of the reaction, and further elevated to 220° C. at the point in time of 33 hours after the start of the reaction. 18 Hours after the start of the reaction, the conversion of cyclohexylamine was 2% and the selectivity for ε-caprolactam was 2%; 26 hours after the start of the reaction, the conversion of cyclohexylamine was 2% and the selectivity for ε-caprolactam was 4%; and 40 hours after the start of the reaction, the conversion of cyclohexylamine was 3% and the selectivity for ε-caprolactam was 4%.

EXAMPLE 28

<Catalyst: SAPO-34 (Phosphate Zeolite)>

146.7 g of water and 95.9 g of a 85% by weight aqueous phosphate solution were mixed together, and thereto was added 169.6 g of aluminum isopropoxide, followed by stirring. 1.6 g of a silica powder was added to the mixture, followed by stirring, to thereby obtain a homogenous mixture. Thereto was added 305.2 g of a 20% by weight aqueous solution of tetraethylammonium hydroxide (($C_2H_5$)$_4$NOH; manufactured and sold by Wako Pure Chemical Industries, Ltd., Japan) and further stirred until a homogeneous mixture was obtained.

The thus obtained homogeneous mixture was transferred to a 1-liter autoclave, followed by hydrothermal synthesis at 150° C. for 133 hours, thereby obtaining a slurry. The obtained slurry was subjected to filtration, and the resultant filtration residue was washed with an ion exchanged water, followed by drying, thereby obtaining a dried product. The dried product was calcined in air at 500° C. for 2 hours, thereby obtaining a calcined, crystalline powder. The obtained crystalline powder was subjected to a powder X-ray diffraction analysis as described above. From the X-ray diffraction pattern, the crystalline powder was confirmed to be silicoaluminophophate SAPO-34. The crystalline powder was further subjected to an energy dispersive X-ray analysis. It was found that the ($P_2O_5+Al_2O_3$)/$SiO_2$ molar ratio of the catalyst was 16.4.

The calcined, crystalline powder (SAPO-34) was added to a 1 N aqueous ammonium nitrate solution to thereby obtain a 10% by weight slurry of SAPO-34, and the obtained slurry was subjected to ion exchange treatment at room temperature for 3 hours. The resultant slurry was subjected to filtration, and the resultant filtration residue was washed with an ion exchanged water, followed by drying at 120° C. for 10 hours, to thereby obtain a dried product. The obtained dried product was subjected to calcination at 530° C. for 3 hours, thereby obtaining an H-type SAPO-34 catalyst.

A reaction was performed in substantially the same manner as in Example 1, except that the obtained catalyst was used as the solid catalyst, the reaction was started at 160° C., the temperature of the reaction vessel was elevated to 180° C. at the point in time of 24 hours after the start of the reaction, and further elevated to 220° C. at the point in time of 33 hours after the start of the reaction. 12 Hours after the start of the reaction, the conversion of cyclohexylamine was 1% and the selectivity for ε-caprolactam was 3%; 30 hours after the start of the reaction, the conversion of cyclohexylamine was 1% and the selectivity for ε-caprolactam was 4%; and 40 hours after the start of the reaction, the conversion of cyclohexylamine was 1% and the selectivity for ε-caprolactam was 3%.

EXAMPLE 29

<Catalyst: Silicalite-1 (Zeolite)>

To 130.0 g of tetraethoxysilane was added 278.2 g of ethanol, and thereto was further added 241.8 g of a 10% by weight aqueous tetrapropylammonium hydroxide solution. The resultant mixture was stirred using a homogenizer at a revolution rate of 5,000 rpm for 20 minutes. Subsequently, the homogenized mixture was transferred to a 1-liter autoclave, followed by hydrothermal synthesis at 100° C. for 5 days, thereby obtaining a slurry. The obtained slurry was subjected to filtration, and the resultant filtration residue was washed with an ion exchanged water, followed by drying at 110° C. for 5 hours, thereby obtaining a dried product. The obtained dried product was subjected to calcination at 530° C. for 3 hours, thereby obtaining a catalyst. The obtained catalyst was subjected to a powder X-ray diffraction analysis as described above. From the X-ray diffraction pattern, the catalyst was confirmed to be silicalite-1.

A reaction was performed in substantially the same manner as in Example 1, except that the obtained catalyst was used as the solid catalyst, the reaction was started at 160° C., the temperature of the reaction vessel was elevated to 180° C. at the point in time of 22 hours after the start of the reaction, and further elevated to 200° C. at the point in time of 32 hours after the start of the reaction. 20 Hours after the start of the reaction, the conversion of cyclohexylamine was 5% and the selectivity for ε-caprolactam was 9%; 30 hours after the start of the reaction, the conversion of cyclohexylamine was 6% and the selectivity for ε-caprolactam was 22%; and 38 hours after the start of the reaction, the conversion of cyclohexylamine was 7% and the selectivity for ε-caprolactam was 28%.

EXAMPLE 30

<Catalyst: Silicalite-1 (Zeolite)>
A reaction was performed in substantially the same manner as in Example 1, except that the catalyst obtained in Example 29 was used as the solid catalyst, and the temperature of the reaction vessel was maintained at 190° C. 10 Hours after the start of the reaction, the conversion of cyclohexylamine was 6% and the selectivity for ε-caprolactam was 30%.

EXAMPLE 31

<Catalyst: Silicalite-2 (Zeolite)>
To 102.0 g of silicon oxide hydrate ($SiO_2 \cdot nH_2O$; manufactured and sold by Wako Pure Chemical Industries, Ltd., Japan) was added 129.7 g of a 10% by weight aqueous solution of tetrabutylammonium hydroxide ($[CH_3(CH_2)_3]_4NOH$; manufactured and sold by Wako Pure Chemical Industries, Ltd., Japan), followed by stirring. Thereto were added 75.0 g of a 28% aqueous ammonia while stirring, followed by addition of 228.1 g of water. The stirring of the resultant mixture was continued at room temperature for 1 hour. The resultant mixture was transferred to a 1-liter autoclave, followed by hydrothermal synthesis at 170° C. for 3 days, to thereby obtain a slurry. The obtained slurry was subjected to filtration, and the resultant filtration residue was washed with an ion exchanged water, followed by drying at 100° C. for 4 hours, thereby obtaining a dried product. The obtained dried product was subjected to calcination at 550° C. for 8 hours, thereby obtaining a catalyst. The obtained catalyst was subjected to a powder X-ray diffraction analysis as described above. From the X-ray diffraction pattern, the catalyst was confirmed to be silicalite-2.

A reaction was performed in substantially the same manner as in Example 1, except that the obtained catalyst was used as the solid catalyst, and the temperature of the reaction vessel was maintained at 195° C. 6 Hours after the start of the reaction, the conversion of cyclohexylamine was 6% and the selectivity for ε-caprolactam was 25%.

EXAMPLE 32

<Catalyst: Silicalite-2 (Zeolite)>
A reaction was performed in substantially the same manner as in Example 1, except that the catalyst obtained in Example 31 was used as the solid catalyst, and the temperature of the reaction vessel was maintained at 215° C. 3 Hours after the start of the reaction, the conversion of cyclohexylamine was 8% and the selectivity for ε-caprolactam was 41%.

EXAMPLE 33

<Catalyst: Silicalite-2 (Zeolite)>
A reaction was performed in substantially the same manner as in Example 1, except that the catalyst obtained in Example 31 was used as the solid catalyst, and the temperature of the reaction vessel was maintained at 230° C. 3 Hours after the start of the reaction, the conversion of cyclohexylamine was 9% and the selectivity for ε-caprolactam was 37%.

EXAMPLE 34

<Catalyst: Silicalite-2 (Zeolite)>
A reaction was performed in substantially the same manner as in Example 1, except that the catalyst obtained in Example 31 was used as the solid catalyst, and the temperature of the reaction vessel was maintained at 250° C. 2 Hours after the start of the reaction, the conversion of cyclohexylamine was 12% and the selectivity for ε-caprolactam was 26%.

EXAMPLE 35

A reaction was performed using the catalyst prepared in Example 15. The reaction vessel used for performing the reaction was a tubular reactor (outer diameter: 25.4 mm, inner diameter: 23.00 mm, length: 700 mm) which was made of SUS316 and which was provided with a sheath tube for inserting a thermocouple therein, wherein the thermocouple was used to measure the temperature of a catalyst layer formed inside the reaction vessel; and a layer of SUS316 fillers for vaporizing cyclohexylamine, which layer is provided above the catalyst layer. The reaction vessel was placed in a heating furnace for heating the reaction vessel, wherein the heating furnace had three heating stages (upper, middle and lower heating stages).

The above-mentioned reaction vessel was charged with 40 g of the catalyst prepared in Example 15. The reaction vessel had attached thereto two traps (1st trap and 2nd trap) for condensing the gaseous reaction mixture obtained from an outlet of the reaction vessel, wherein each of the traps were provided with a jacket and the 1st and 2nd traps were maintained at 70° C. and 5° C., respectively. After purging the reaction vessel with nitrogen gas, the reaction vessel was heated to and maintained at 215° C. The reaction was started by feeding liquid cyclohexylamine, oxygen and nitrogen into the reaction vessel, wherein cyclohexylamine was fed at 25° C. at a flow rate of 0.1 ml/min, and oxygen and nitrogen were fed at 28 cc/min and 372 cc/min, respectively. The composition of the mixture of cyclohexylamine, oxygen and nitrogen around the inlet of the catalyst layer became: cyclohexylamine=5.1% by volume, oxygen=6.6% by volume, and nitrogen=88.3% by volume. The SV value was 272 $h^{-1}$.

The reaction was continued for 48 hours, and 268 g of a liquid reaction mixture was collected in total from the 1st and 2nd traps. The collected reaction mixture contained 26 g of ε-caprolactam. After repeating the distillation of the reaction mixture, ε-caprolactam was purified by crystal deposition using cyclohexane as a solvent. The purity of the thus obtained ε-caprolactam, as measured by means of GC, was 99.9%.

EXAMPLE 36

<Synthesis of Cyclohexylamine by an Amination Reaction of Cyclohexanol>

To an aqueous solution obtained by dissolving 47 g of copper sulfate trihydrate and 16 g of nickel nitrate hexahydrate in 250 ml of water was added, followed by stirring. The resultant mixture was heated to and maintained at 80° C. by means of a water bath, and thereto was dropwise added 250 ml of an aqueous sodium carbonate solution (containing 42 g of sodium carbonate) over 2 hours while stirring. The resultant mixture was subjected to aging for 5 hours, to thereby obtain a slurry. The obtained slurry was subjected to filtration, and the resultant filtration residue was repeatedly washed with warm water, followed by drying at about 100° C. for one day, thereby obtaining a dried product. The dried product was pulverized using a mortar. The resultant pulverized product was charged into a quartz glass tube and calcined in air at 350° C. for 3 hours, thereby obtaining a copper-nickel/γ-alumina catalyst.

The above-obtained copper-nickel/γ-alumina catalyst was shaped into particles and charged into a tubular reactor made of stainless steel. Hydrogen gas was fed into the reactor at a rate of 150 ml/min, while maintaining the temperature of the catalyst phase at 350° C., to thereby perform an activation treatment of the catalyst for 3 hours. After the activation treatment, the temperature of the reactor was lowered to 180° C., and into the reactor was fed a gaseous feedstock mixture (which had a cyclohexanol:ammonia:hydrogen molar ratio of 1:5:3). The feeding of the gaseous feedstock mixture was performed under atmospheric pressure and under conditions wherein the LSV value became 0.1 liter/liter of catalyst/hour. The reaction was continued for 5 hours. The reaction product was analyzed by GC, and it was found that the conversion of cyclohexanol was 99.0% and the selectivity for cyclohexylamine was 96.1%.

EXAMPLE 37

<Recycling of the By-Products of the Oxidation Reaction of Cyclohexylamine to the Amination Reaction System>

50 g of cyclohexanol was mixed with 10 g of a dilute obtained in Example 35 during the distillation performed to purify ε-caprolactam separated from the collected reaction mixture, to thereby obtain a mixture. The dilute contained the following by-products: 22% of cyclohexanone, 74% of N-cyclohexylidene cyclohexylamine and 4% of other compounds. Using the obtained mixture, an amination reaction was performed under the same conditions as used in Example 36. As a result, it was found that the conversion of the by-products was 98.3% and the selectivity for cyclohexylamine was 97.1%.

INDUSTRIAL APPLICABILITY

The method of the present invention not only prevents the by-production of ammonium sulfate which is of little commercial value, but also needs no cumbersome operations involved in conventional methods for producing a lactam, such as synthesis of hydroxylamine salt (which can be obtained only by a process involving complicated steps) and circulation of a buffer solution, and involves no step of producing intermediate oxime, which should be followed by an oxime purification operation, and, hence, a lactam can be produced from an alicyclic primary amine very easily.

The lactam produced by the method of the present invention is a useful compound as a raw material for polymers, pharmaceuticals, agricultural chemicals and the like in the field of organic chemical industry. Especially, in the case where the lactam is ε-caprolactam, it is used for producing fibers and resins and it is useful as a raw material for nylon 6.

What is claimed is:

1. A method for producing a lactam, which comprises subjecting an alicyclic primary amine to an oxidation reaction in the gaseous phase in the presence of molecular oxygen and a catalyst comprising a silicon oxide, to thereby obtain a lactam, and separating said lactam from a reaction system of said oxidation reaction.

2. The method according to claim 1, wherein said catalyst further comprises at least one element selected from the group consisting of lithium, sodium, potassium, rubidium, cesium, magnesium, calcium, strontium, barium, titanium, zirconium, vanadium, niobium, tantalum, molybdenum, tungsten, manganese, iron, cobalt, nickel, copper, zinc, silver, boron, aluminum, gallium, tin, phosphorus, antimony and bismuth.

3. The method according to claim 1, wherein said catalyst is a zeolite.

4. The method according to claim 3, wherein said zeolite is selected from the group consisting of silicalite-1 and silicalite-2.

5. The method according to claim 1, wherein said catalyst comprises an amorphous silicon oxide as said silicon oxide.

6. The method according to claim 5, wherein said catalyst further comprises aluminum.

7. The method according to claim 5, wherein said amorphous silicon oxide has mesopores.

8. The method according to claim 7, wherein said amorphous silicon oxide having mesopores is selected from the group consisting of MCM-41 and HMS.

9. The method according to claim 7, wherein said amorphous silicon oxide having mesopores is produced by adding to a silicon alkoxide a quaternary ammonium salt.

10. The method according to claim 9, wherein said quaternary ammonium salt is cetyltrimethyl ammonium salt.

11. The method according to any one of claims 1 and 2 to 10, wherein, said alicyclic primary amine is obtained by subjecting to an amination reaction at least one compound selected from the group consisting of an alicyclic alcohol and an alicyclic ketone.

12. The method according to claim 11, wherein at least a part of one or more by-products formed in said oxidation reaction is recycled to a reaction system of said amination reaction.

13. The method according to claim 1, wherein said alicyclic primary amine is cyclohexylamine, and said lactam is ε-caprolactam.

14. The method according to claim 11, wherein said at least one compound selected from the group consisting of an alicyclic alcohol and an alicyclic ketone is selected from the group consisting of cyclohexanol and cyclohexanone, said alicyclic primary amine is cyclohexylamine, and said lactam is ε-caprolactam.

15. A catalyst for use in producing a lactam by subjecting an alicyclic primary amine to an oxidation reaction, which comprises a silicon oxide.

16. The catalyst according to claim 15, which further comprises at least one element selected from the group consisting of lithium, sodium, potassium, rubidium, cesium, magnesium, calcium, strontium, barium, titanium, zirconium, vanadium, niobium, tantalum, molybdenum, tungsten, manganese, iron, cobalt, nickel, copper, zinc, silver, boron, aluminum, gallium, tin, phosphorus, antimony and bismuth.

17. The catalyst according to claim 15, which is a zeolite.

18. The catalyst according to claim 17, which is a zeolite selected from the group consisting of silicalite-1 and silicalite-2.

19. The catalyst according to claim 15, which comprises an amorphous silicon oxide as said silicon oxide.

20. The catalyst according to claim 19, which further comprises aluminum.

21. The catalyst according to claim 19, wherein said amorphous silicon oxide has mesopores.

22. The catalyst according to claim 21, wherein said amorphous silicon oxide having mesopores is a selected from the group consisting of MCM-41 and HMS.

23. The catalyst according to claim 21, wherein said amorphous silicon oxide having mesopores is produced by adding to a silicon alkoxide a quaternary ammonium salt.

24. The catalyst according to claim 23, wherein said quaternary ammonium salt is cetyltrimethyl ammonium salt.

\* \* \* \* \*